(12) United States Patent
Kánai et al.

(10) Patent No.: US 6,191,161 B1
(45) Date of Patent: Feb. 20, 2001

(54) PROLYLENDOPEPTIDASE INHIBITORS

(75) Inventors: Károly Kánai; Sándor Erdö; Andrea Szappanos; Judit Bence; István Hermecz, all of Budapest; Györgyné Szvoboda, Dunakeszi; Sándor Bátori; Gergely Héja, both of Budapest; Mariá Balogh, Dunakeszi; Ágnes Horváth, Budapest; Judit Sipos, Budapest; Bodor Veronika Bártáne, Budapest; Zsolt Párkányi, Budapest; Viktor Lakics, Budapaest; Péter Molnár, Kistarcsa, all of (HU)

(73) Assignee: Chinoin Gyogyszer es Vegyeszeti, Budapest (HU)

( * ) Notice: Under 35 U.S.C. 154(b), the term of this patent shall be extended for 0 days.

(21) Appl. No.: 09/011,703
(22) PCT Filed: Jul. 26, 1996
(86) PCT No.: PCT/HU96/00041
§ 371 Date: Apr. 17, 1998
§ 102(e) Date: Apr. 17, 1998
(87) PCT Pub. No.: WO97/07116
PCT Pub. Date: Feb. 27, 1997

(30) Foreign Application Priority Data

Aug. 17, 1995 (AU) .................................. P9502426

(51) Int. Cl.$^7$ .......................... A61K 31/40; C07D 209/02
(52) U.S. Cl. ............................................. 514/414; 548/465
(58) Field of Search .................................... 548/524, 465; 514/414

(56) References Cited

FOREIGN PATENT DOCUMENTS

0232849A2    8/1987  (EP) .

OTHER PUBLICATIONS

Yoshimoto et al., *Biochemica et Biophysica Acta*, 569 pp. 184–192 (1979).
Toide et al., *J. Pharm. Exp. Therapeutics*, 274, pp. 1370–1378 (1995).
Riedel et al., *Drugs and Aging*, 8(4), pp. 245–274 (1998).
Kowall et al., *Proc. Natl. Acad. Sci. USA*, vol. 88, pp. 7247–7251 (Aug. 1991).
O'Leary et al., *J. of Neurochem.*, vol. 65, No. 3, pp. 953–963 (1995).
Atack et al., *European Journal of Pharmacology*, 205, pp. 157–163 (1991).
Arai et al., *Chem. Pharm. Bull.*, 41(9), pp. 1583–1588 (1993).
König et al., *Chem. Ber*, pp. 788–798 (1970).

*Primary Examiner*—Robert W. Ramsuer
*Assistant Examiner*—Ebenezer Sackey
(74) *Attorney, Agent, or Firm*—Birch, Stewart, Kolasch & Birch, LLP

(57) ABSTRACT

The present invention relates to new prolylendopeptidase inhibitors of general formula (I).

9 Claims, 5 Drawing Sheets

A—B—C—D—L

I

1

2

3

1a

2a

3a

4

5

6

7

8

9

10

11a

11b

12

12a

12b

13

13a

14

15

16

17

18

19

19a

20

20a

21

22

23

23a

23b

24

25

25a

26

27

28

28a

28b

29

29a

30

31

32

32a

33

34

35

36

37

38

39

40

41

42

43

43a

44

45

46

47

48

49

A—B—OH

[II]

H—CDL

[III]

PROLYLENDOPEPTIDASE INHIBITORS

Figure 1:
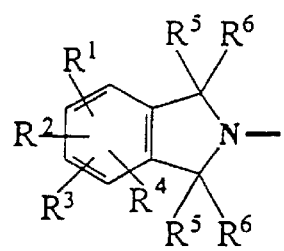
Figure 1:
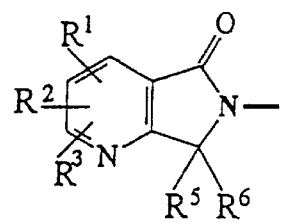
Figure 1:
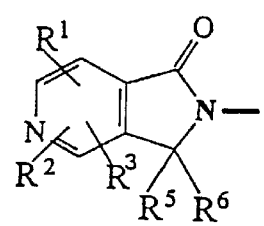
Figure 1:
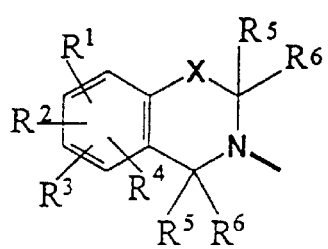
Figure 1:
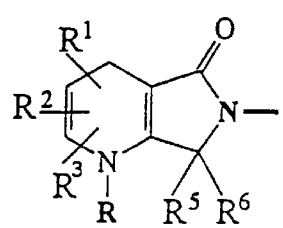
Figure 1:
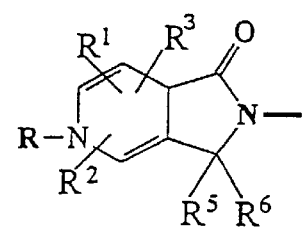
Figure 1:
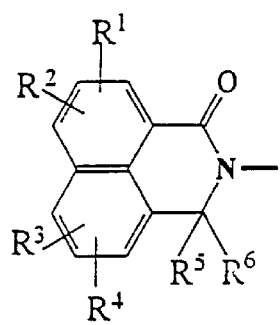
Figure 1:
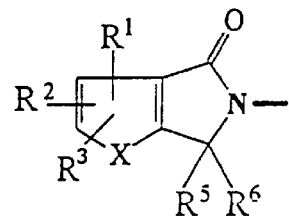
Figure 1:
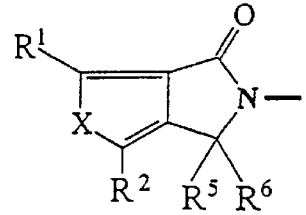
Figure 1:
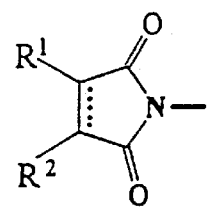
Figure 1:
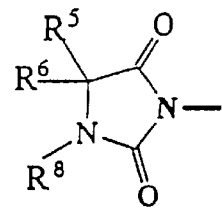
Figure 2:
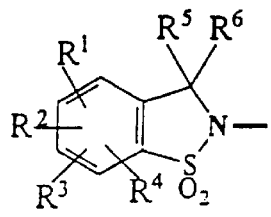
Figure 2:
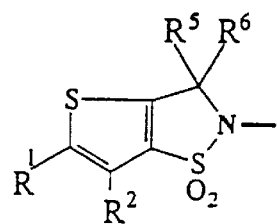
Figure 2:
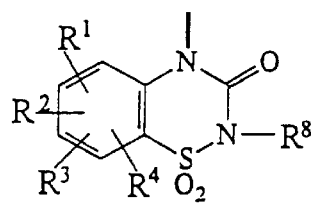
Figure 2:
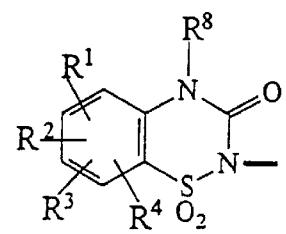
Figure 2:
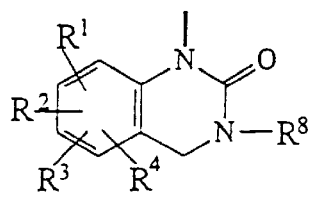
Figure 2:
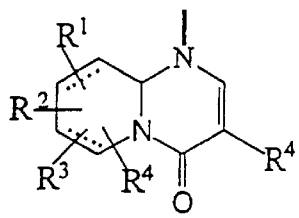
Figure 2:
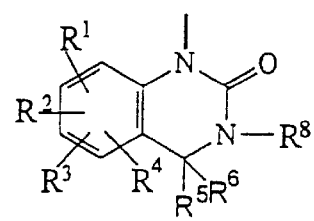
Figure 2:
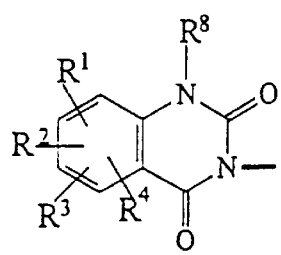
Figure 2:
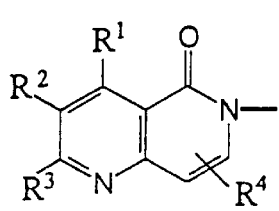
Figure 2:
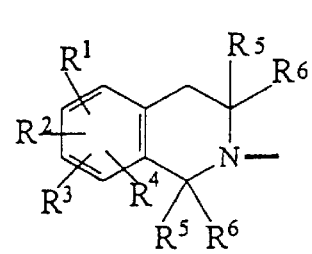
Figure 2:
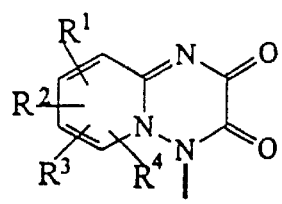
Figure 2:
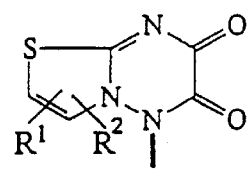
Figure 3:
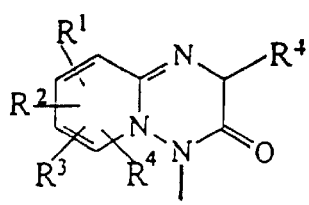
Figure 3:
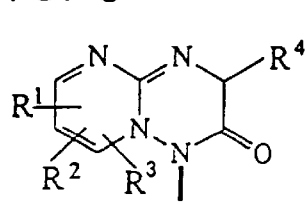
Figure 3:
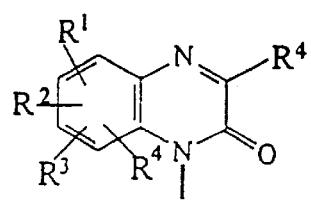
Figure 3:
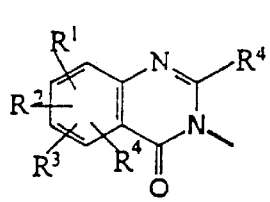
Figure 3:
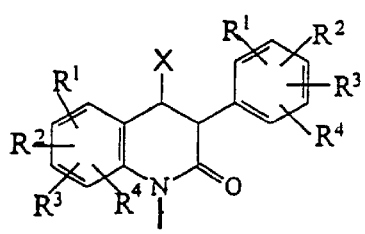
Figure 3:
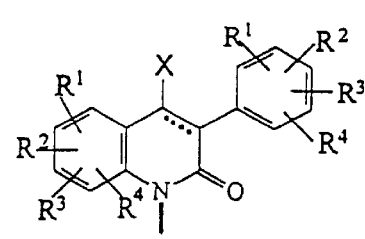
Figure 3:
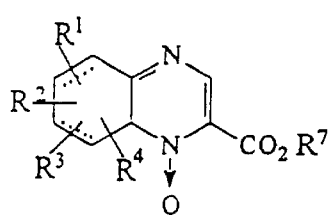
Figure 3:
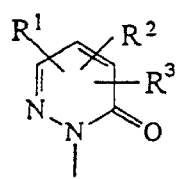
Figure 3:
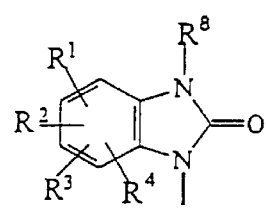
Figure 3:
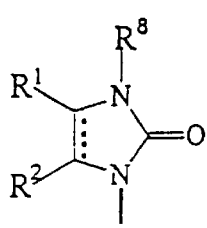
Figure 3:
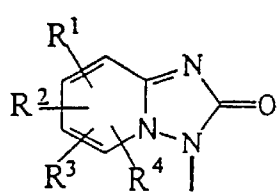
Figure 3:
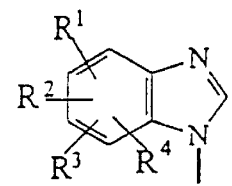
Figure 3:
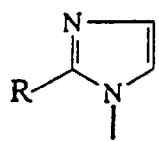
Figure 3:
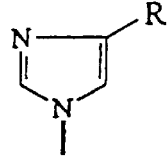
Figure 3:
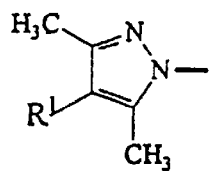
Figure 3:
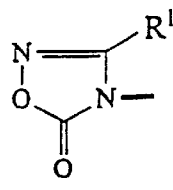
Figure 4:
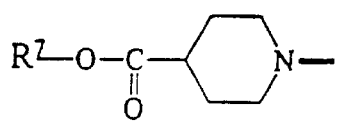
Figure 4:
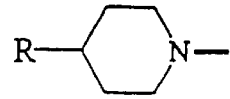
Figure 4:
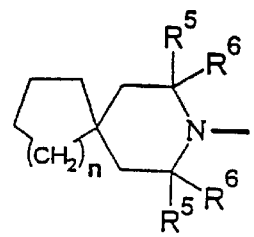
Figure 4:
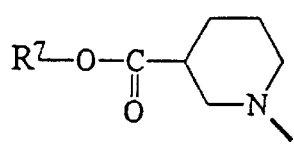
Figure 4:
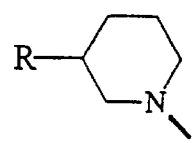
Figure 4:
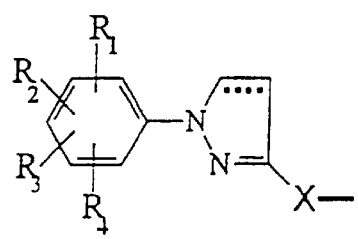
Figure 4:
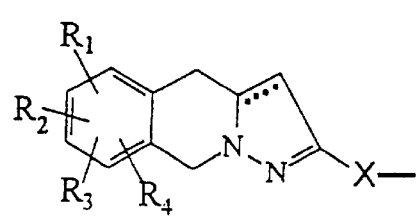
Figure 4:
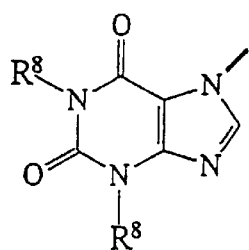
Figure 4:
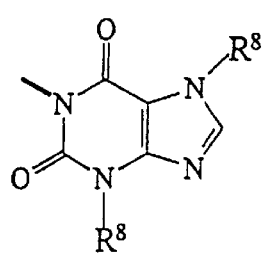
Figure 4:
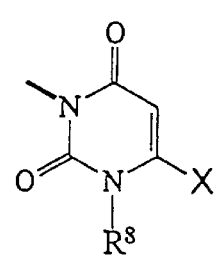
Figure 4:
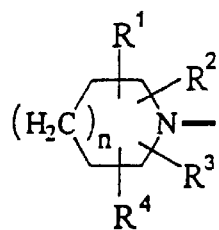
Figure 4:
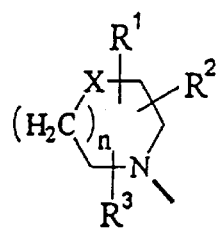
Figure 4:
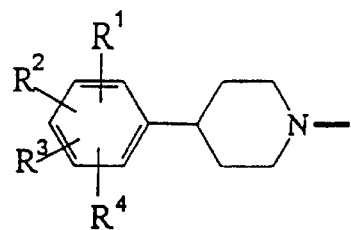
Figure 5:
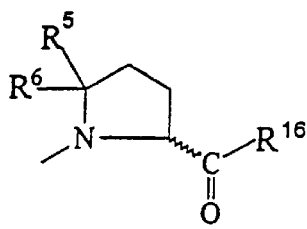
Figure 5:
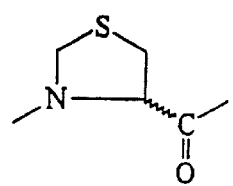
Figure 5:
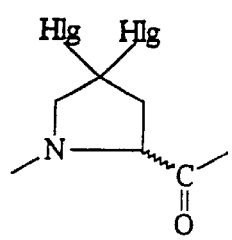
Figure 5:
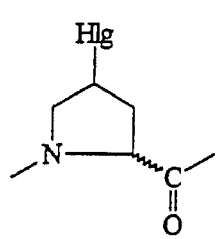
Figure 5:
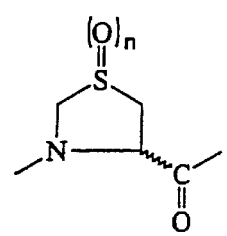
Figure 5:
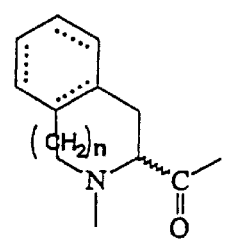
Figure 5:
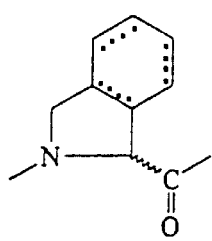
Figure 5:
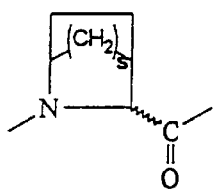
Figure 5:
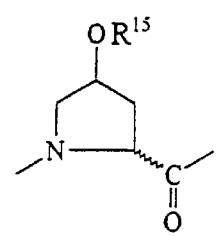
Figure 5:
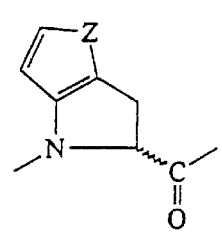
Figure 5:
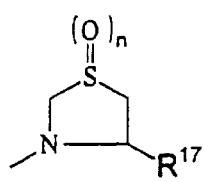
Figure 5:
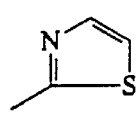
Figure 5:
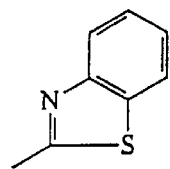
Figure 5:
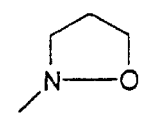

This application is the national phase under 35 U.S.C. §371 of prior PCT International Application No. PCT/HU96/00041 which has an International filing date of Jul. 26, 1996 which designated the United States of America, the entire contents of which are hereby incorporated by reference.

The present invention relates to new compounds of the general Formula (I), to pharmaceutical compositions containing them, and to the process for the preparation of these compounds. A further aspect of our present invention is the use of the new compounds of the general formula I for the treatment of CNS diseases by inhibition of certain enzymes described later on on this page.

Because of the incidence and social consequences of diseases of the central nervous system accompanied with amnesia, dementia and the progressive decline of cognitive and intellectual functioning for example Alzheimer disease, AIDS dementia, senile dementias of various origin (hypoxia, ischaemia) there are significant demands for new pharmaceuticals for treating and preventing the diseases mentioned above.

Prolyl endopeptidase PE or PEP is a post-proline cleaving enzyme (PPCE). It is widespread in mammalian species and can be found in various organs of the body. The level of the enzyme is the highest in the brain, testis and skeletal muscle (Yoshimoto T., Ogita K., Walter, R., Koida M. and Tsuru D.: Biochim. Biophys. Acta, 569, (1979), 184–192).

PEP has some important role in memory process due to the fact that its substrates are biologically active neuropeptides (substance P, thyrotropin-releasing hormone, $Arg^8$-Vasopressin). These neuropeptides exert characteristic pharmacological effects on the central nervous system: they are capable of changing the performance of animals and humans in learning and memory tasks (Toide K., Iwamoto Z., Fujiwara T., and Abe H.: J. Pharm. Exp. Therapeutics, 274, (1995), 1370–1378; Riedel W. and Jolles J. Drugs & Aging, 8, (1996), 245–274). The neuropeptide sustance P prevents β-amyloid-induced neuronal loss and expression of Alz-50 proteins in cerebral cortex (Kowall N., Beal M. F., Busciglio J., and Duffy L. K.: Proc. Natl. Acad. Sci., 88, (1991), 7247–7251). In brains of patients with Alzheimer's disease, it is well known that the cerebral ACh content decreased and the cerebral function suffers severe damage (O'Leary R. and O'Connor B.: J. Neurochem., 65, (1995), 953–963). A PEP inhibitor through the increasing the level of TRH could induce ACh release in the brain which should result in a better cognitive performance. It can be supposed that a highly specific PEP inhibitor could prove to be useifilul in the treatement of diseases of central nervous system in neurodegenerative illnesses.

The new PEP inhibitor as a new drug would be a
1. nootropic drug having memory enhancing and anti-amnestic effect and could be used in treatment of age-related cognitive decline;
2. neuropotective agent useful in therapy of
    a., acute events (ischemia/hypoxia)
    b., progressive neurodegenerative disorders
       Alzheimer's disease
       AIDS dementia
       Huntington's disease Senile dementia and Alzheimer's disease become serious and fastly outgrowing problem of the aging population and a PEP inhibitor could be useful for the general treatment of the above mentioned serious diseases.

We set ourselves the task of preparing new PEP-inhibitors displaying advantageous characteristics which could serve as active ingredients of new drugs. By advantages we mean over a strong PEP—inhibitory effect, selectivity, easily transfer through the blood-brain barrier, a long half-life, good oral resorption, enchanced chemical and biological stability and advantageous therepautical profile including lowser toxicity and low probability of side effects.

During the synthesis and biological examination of numerous new compounds we found that new compounds of the general formula (I) wherein A means an onefold or manifold substituted or unsubstituted organic cyclic group containing one nitrogen atom with one free valency and optionally one or more further heteroatom selected from a group consisting of nitrogen atom, sulfuratom or oxigenatom, especially a group having the general formula (1), (1a), (2), (2a), (3), (3a), (4), (5), (6), (7), (8), (9), (10), (11a), (11b), (12), (12a), (12b), (13), (13a), (14), (15), (16), (17), (18), (19), (19a), (20), (20a), (21), (22), (23), (23a), (23b), (24), (25), (25a), (26), (27), (28), (28a), (28b), (29), (29a), (30), (31), (32), (32a), (33), (34), (35), (36)—wherein R means hydrogenatom alkyl group of 1–4 carbon atoms or aryl or aralkyl group of 6–12 carbon atoms;

$R^1$, $R^2$, $R^3$ and $R^4$ mean independently from each other hydrogen atom, halogen atom, hydroxyl group, straight chain or branched chain alkvl or alkenyl- or alkinyl or alkoxy- or alkenyloxy- or alkinyloxy groups containing 1–6 carbon atoms, nitro-group, amino group, monoalkylamino or monoacylamino group of 1–12 carbon atoms, dialkylamino- or diacylamino group of 2–24 carbon atoms—where the acyl group is an alkyl, aralkyl, cycloalkyl or aryl type-, cyano group, mercapto group, carboxyl group, esterified carboxyl group of 2–7 carbon atoms, hydroxyalkyl group of 1–6 carbon atoms, acyl group of 1–7 carbon atoms, acyloxy group of 1–7 carbon atoms, phenyl or benzyl group, anilino group, benzoyl group, phenoxy group, benzyloxy group, isocyanato group, isothiocyanato group, alkylthio group of 1–6 carbon atoms, sulfamino or sulfamoyl group, thiocyanato or cyanato group;

$R^5$ and $R^6$ mean independently from each other hydrogen atom, hydroxyl group phenyl group or alkyl group of 1–4 carbon atoms or $R^5$ and $R^6$ together mean oxo group;

$R^7$ means alkyl group of 1–6 carbon atoms;

$R^8$ means hydrogen atom or alkyl group of 1–6 carbon atoms or aralkyl group of 7–10 carbon atoms;

the dotted line means an optional chemical bond;

n is zero 1, 2 or 3;

X means —$CH_2$— group, —NH— group, carbon atom, hydrogen atom, oxygen atom or amino group; or A means an R—Y—N=group or

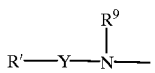

group—wherein R' means alkyl group of 1–6 carbon atoms, aralkyl group of 7–10 carbon atoms, diphenylmethyl group, alkoxy group, arylalkyloxy group of 7–10 carbon atoms, or phenyl- or phenoxy or phenylalkyl group containing 7–10 carbon atoms or phenylalkyloxy group containing 7–10 carbon atoms optionally substituted with halogen atoms or alkyl groups of 1–4 carbon atoms or nitro groups; Y means chemical bond or oxo-, sulfonyl- or sulfinyl group, $R^9$ means hydrogen atom or alkyl group of 1–4 carbon atoms;

—with the proviso that in the case of formulas (20) and (33) X cannot mean —CH$_2$— group, —NH— group, oxygen atom or sulfur atom and in the case of formulas (30) and (31) X cannot mean —CH$_2$— group, oxygen atom or sulfur atom or amino group;

B means

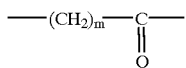

group—wherein m is an integer of 1 to 21; or

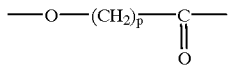

group wherein p is an integer of 1 to 3; or

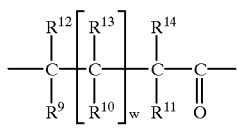

group—wherein $R^9$, $R^{10}$, $R^{11}$, $R^{12}$, $R^{13}$ and $R^{14}$ mean independently from each other hydrogen alkyl or alkoxy group of 1–6 carbonatoms, halogen, amino group optionally substituted with one or two alkyl group of 1–6 carbonatoms; or phenyl, phenoxy, aryl-alkyl group of 7–12 carbonatoms or aryl-alboxy group of 7–12 carbonatoms each of them optionally containing 1, 2 or 3 same or different substituents identical to $R^1$, $R^2$, $R^3$ or $R^4$; or two of $R^9$, $R^{10}$, $R^{11}$, $R^{12}$, $R^{13}$ and $R^{14}$ mean together an oxo or epoxy group or further chemical bond or four of them mean together two further chemical bonds and the remaining groups stand for hydrogen atoms; or $R^9$, $R^{10}$, $R^{11}$, $R^{12}$, $R^{13}$ and $R^{14}$ mean together with the chain carbonatoms a saturated or unsaturated homocycle containing 3–8 carbon atoms or a saturated or unsaturated heterocycle containing 2–7 carbon atoms and a nitrogen or sulfur or oxygen atom, to which optionally an aromatic ring of 6–10 carbon atoms is condensed; and w is zero or 1;

C means prolyl group or one of the groups of formula (37), (38), (39), (40) or (41)—where n is zero or 1 or 2, Hlg means fluorine, chlorine, bromine, or iodine atom;

$R^5$ and $R^6$ mean independently from each other hydrogen atom, hydroxyl group phenyl group or alkyl group of 1–4 carbonatoms or $R^5$ and $R^6$ together mean oxo-group;

$R^{16}$ means an alkoxy group of 1–4 carbon atoms, or —NH—CH$_2$—CN group, or —NH—CH$_2$—CO$_2$R$^7$ group—where $R^7$ is defined as above; or D or L structural unit; or one of the group of the formula (42) or (43) or (43a)—where the dotted line means a chemical bond optionally present-, s is 1, 2 or 3- or a group of the formula (44)—wherein $R^{15}$ means hydrogen atom, alkyl group of 1–6 carbon atoms, phenyl or naphthyl group; or a group of the formula (45)—wherein Z means NH— group, oxygen atom or sulfur atom;

D means a covalent chemical bond or prolyl- or thioprolyl group, or one of groups of formula (37) or (38), (39), (40) or (41);

L means pyrrolidino- or 2-cyanopyrrolidino, thiazolidino or 2-cyano-thiazolidino or piperidino group optionally substituted with one halogen atom or geminally with two halogen atoms; or a group of the formula (46)—where $R^{17}$ means hydrogen atom or cyano group, n is 0, 1 or 2; or a group of the formula (47) or (48) or (49);

and optical, cis-trans, geometric isomers, epimers, tautomers, salts, prodrugs and human and mammalian metabolites of them have significant prolylendopeptidase inhibiting effect and they show one or more advantages mentioned above. Some preferred groups of compounds of the general formula (I) are as defined claimed in claims 3, 8 and 9.

The meaning of "onefold or manifold substituted or unsubstituted organic cyclic group containing one nitrogen atom with one free valency and optionally one or more further heteroatom(s) selected from a group consisting of nitrogen atom, sufuratom or oxigen atom" in case of A covers all know monocyclic or polycyclic group satisfying above definition.

In case of a polycyclic group the rings may be condensed and/or may be in spirocyclic position. Some representatives of above cyclic groups are depicted in formulas, (1), (1a), (2), (2a), (3), (3a), (4), (5), (6), (7), (8), (9), (10), (11a), (11b), (12), (12a), (12b), (13), (13a), (14), (15), (16), (17), (18), (19), (19a), (20), (20a), (21), (22), (23), (23a), (23b), (24), (25), (25a), (26), (27), (28), (28a), (28b), (29), (29a), (30), (31), (32), (32a), (33), (34), (35), (36).

In the definitions of general formula (I) "alkyl group of 1–6 carbonatoms" means a straight chain or branched alkyl group having 1 to 6 carbonatoms such as methyl, ethyl, propyl, butyl, isobutyl, sec-butyl, tert-butyl, pentyl, neopentyl and hexyl. The "aryl group of 6–10 carbonatoms" means for example phenyl, tolyl or naphthyl groups.

The "aralkyl group of 6–10 carbonatoms" means for example benzyl-, 1-phenyl-ethly-, 2-phenyl, ethly-, 1-phenyt-propyl-groups. The alkenyl group of 1–6 carbon atoms means a straight chain or branched alkenyl group such as vinyl, allyl, methaorlyl, crotyl, 3-butenyl, 2-pentenyl-, 4-pentenyl-, 2-hexenyl-, 5-hexenyl. The "alkynyl group of 1–6 carbon atoms" means a straigh-chain or branched alkynyl group such as ethynyl, propargyl, 2-butynyl-, 3-butynyl, 2-pentynyl, 4-pentynyl, 2-hexynyl 5-hexynyl 4-methyl-2-hexynyl.

The cycloalkyl part of the "acyl group of 1–12 carbonatoms" means for example cyclopropyl, cyclobutyl, cyclopentyl, cyclohexyl, cvcloheptyl or cyclooctyl group. These definitions may be used in case of alkvloxy, alkenyloxy-, alkymyloxy, aryloxy,aralkyloxy, phenylalkyloxy or alkylamino or acylamino groups.

We have examined the PEP—inhibitory activity and the biological stability of the compounds characterised by formula (I) applying the following methods:

PEP Activity Measurement on Rat Brain Extract:

After removal of the cerebellum whole brain of male (Sprague-Dawley, 180–200 g) rats was homogenized in a double volume of 0.1 M Tris-HCl, 1 mM EDTA buffer, pH=7.5 (PEP buffer). The homogenate was centrifuged for 30 min. at 4° C. at 40000 g and the supernatant, containing the enzyme, was collected. The pellet was resuspended in the same volume of buffer as in the first case and centrifuged again under the same conditions. The two supernatants were pooled and stored in 1 ml aliquots at −70° C. (for at least 3 months). The supernatant was thawn just before activity measurement and diluted in a 1:15 ratio with PEP buffer. The enzyme activity was measured by using flurometric method described by J. R. Atack et al. (Eur J. Pharmacol., 205, (1991), 157–163). Enzyme reaction was performed at room temperature for 15 minutes in the presence of 62.5 $\mu$M Z-glycyl-prolyl-7-amino-4-methyl-coumarin (Bachem Biochem.) as a highly specific synthetic substrate of the PEP. The inhibitory effect of compounds was tested under the same conditions in the presence of 100 to 0.001 nM compound. The formation of 7-amino-4-methyl-coumarin was detected spectrofluorometrically at 370 nm exitation and 440 nm emission wavelength. The 50% inhibition concentration of the compounds ($IC_{50}$) were calculated by curve fitting of the % inhibition of the enzyme versus inhibitor concentration (M) using Hill-equation. $IC_{50}$ values of the compounds of the general formula (I) are in the range of 100 nM–1 pM.

Pig Brain PEP Activity Measurement

Purified pig brain prolyl endopeptidase was a kindly gift of László Polgár (Enzymnology Institute of the Hungarian Academy of Sciences). Enzyme solution was diluted in the reaction mixture 400000 times. Measurements were performed under the same conditions as in the case of the in vitro measurements on rat brain preparation. The compounds of the general Formula I were shown to be also active on pig brain PEP activity.

In Vitro Metabolism Studies

The biological stability of prolyl endopeptidase inhibitors was studied in mouse, rat and human (preparation of the Central Chemistry Institute of The Hungarian Academy of Sciences) liver microsomal preparation. Mouse and rat livers were pooled and homogenized in 4-fold volume Tris-HCl buffer (pH 7.4) containing 1.15% KCl and 1 mM EDTA The homogenates were centrifuged for 30 minutes at 10000 g, the supernatants were further ultracentrifuged for 1 hour at 105000 g. Pellets were rehomogenized and ultracentrifugation was repeated. The pellets were re-homogenized again and were diluted with buffer to a final volume of 0.5 g liver/ml. Sample were frozen in 2 ml aliquots at –80 ° C. Preparations were characterized for cytochrome P450 isoenzyme activities.

New inhibitors of the general formula (I) were tested under the following conditions: Reaction mixture contained 2 mg of liver microsomal protein, 0.1M Tris-HCl buffer (pH=7.4), 2 mM NADP, 20 mM glucose-6-phosphate disodium salt, 10 mM $MgCl_2$ 5 U glucose-6-phosphate dehydrogenase and 50 $\mu$M PEP inhibitors in a final volume of 1.5 ml. After 0, 10, 20, 40 min incubation times, reaction was terminated by addition of acetonitrile. Samples were centrifuged at 3000 rpm for 10 minutes. The supernatant was analyzed by HPLC (Supelcosil C18). The unchanged substrate amount was determined and half-life of compounds were calculated.

Some compounds of the general formula I had half-life on human liver microsomes of more than 7 hours. Such good biological stability is in favour of an long lasting effect in vivo and is an advantage over other peptidic-type PEP-inhibitors which are known to be biologically unstable.

The published European Patent Application No. 0 232 849 A2 describes numerous PEP-inhibitor including SUAM-1221 (N-[N-($\gamma$-phenyl)butyryl-L-prolyl] pyrrolidine). The compounds of the general formula (I) exert high inhibition activity on prolyl endopeptidase and it is greater than that of above reference compound SUAM-1221 measured in our above described test-system:

| Compounds | $IC_{50}$ (M) rat brain extract |
|---|---|
| Example 123 | $2.78 \cdot 10^{-10}$ |
| Example 31 | $3.60 \cdot 10^{-10}$ |
| Example 171 | $4.51 \cdot 10^{-10}$ |
| SUAM-1221 | $3.12 \cdot 10^{-8}$ |

The preparation of compounds of the general formula (I) is carried out by methods well known from the literature or by obvious chemical equivalents thereof relating to the synthesis of peptide type substances.

The A and B units of compounds of the general formula A—B—C—D—L (I)—where the meanings of A, B, C, D, and L are as described above—are coupled by the reaction of the appropriate acid anhydride or other activated acid and derivative aud an amine, yielding compounds of the general formula (II)—where the meanings of A and B are as described above. The coupling of units C and D happens likewise by coupling the appropriate activated acid derivative e.g. acid anhydride and an amine. The coupling of units CD and L to yield compounds of the general formula (III)—where the meanings of CD and L are as described above—is carried out by reacting the appropriate mixed anhydride and amine resp. ester and metallo-organic compound.

The starting compounds corresponding to units A, B, C, D, and L are commercially available or readily producible by known transformation of them or as described in Chem Pharm. Bulletin 41 (9) p 1583–1588 (1993.)

We have prepared the compounds of general formula (I) by reacting activated derivatives of compounds of the general formula (II) with compounds of the general formula (III) under conditions of amide coupling usual in peptide chemistry. The activated derivatives of compounds having general formula (II) could be e.g. acid chlorides, which can be synthesized by applying halogenating agents (e.g. thionyl chloride). Active esters can be produced by 1-hydroxylbenzotriazol in the presence of N,N'-dicyclohexylcarbodiimid (Chem. Ber. 103, 788/1970/). Mixed anhydrides can be produced by—ester of chlorforrmic acid or by pivaloyl chloride (Methoden der S Organischen Chemie (Houben-Weyl) Band XV/2 Synthese von Peptiden, Georg Thieme Verlag, Stuttgart, 1974).

The coupling reaction can favourably be carried out in organic solvent preferably (at a temperature between –25° C. and the boiling point of the reaction mixture). Use of acid binding agents e.g. organic amines is favourable during the reaction.

The compounds of the general formula (I), can be purified, if appropriate, by a conventional purification technique, the isomers of which are separated, if desired, by a conventional separation technique and which are converted, if necessary; to their addition salts with a pharmaceutically acceptable acid.

Pharmaceutically acceptable acids may be for example hydrochloric, sulfuric, tartaric, fumaric methansulfonic acid and the like.

Another subject of the present invention is pharmaceutical compositions containing, as active principle, at least one compound of general formula (I) or one of its addition salts with a pharmacologically acceptable acid, alone or in combination with one or more inert and nontoxic excipients or vehicles.

Mention may more particularly be made, among pharmaceutical compositions according to the invention, of those which are suitable for oral, parenteral rectal or nasal administration, simple or sugar-coated tablets, sublingual tablets, injectable compositions, infusions, packets, gelatin capsules, suppositories, creams, ointments, dermal gels, and the like.

The dose varies according to the age and weight of the patient, the nature and the severity of the ailment and on the administration route.

The latter can be oral, nasal, rectal or parenteral. The unit dose generally varies between 0,1 and 50 mg/body weight kg for a treatment taken 1 to 3 times per 24 hours.

The invention will be fuirther clarified by the following, tabular, non-limiting examples in greater detail and by a detailed process description in case of the example 4. Other embodiments of the invention will be apparent to the person skilled in the art from a consideration of this specification or practice of the invention disclosed herein.

EXAMPLES

Description of the Preparation of Compound Depicted in Example 4 (Table 1)

To a solution prepared by dissolving 1,17 g (5,0 mM) 4-phtalimido-butyric acid and 0,56 g (5,5 mM) triethylamin in 20 ml chloroform 0,61 g (5,0 mm) pivaloylchlorid were dropped at −15° C. under stirring. The reaction mixture was stirred for 1 hour at the above temperature and then a solution prepared by dissolving 1,03 g (5,0 mM) L-prolyl-pyrrolidin-hydrochloric acid salt in a mixture of 5 ml chloroform and 1,5 ml (1,1 g, 11,0 mM) triethylamine were dropwise added to it. Reaction mixture was stirred at room temperature for 4 hours, then it was washed successively with water, 30% cc. citric acid solution, saturated aqueous sodium bicarbonate solution, water and with saturated sodium chloride solution. The organic phase was dried on calcinated magnesium sulfate and it was evaporated. Crystallisation of the residue from a mixture of 5 ml chloroform and 10 ml petrolether yielded 1,1 g (53%) N-(4-phtalimido-butanoyl)-L-prolyl-pyrrolidin which melted at 148–149° C. The compounds of the general formula I were synthetised by the method as explained above starting from the corresponding compounds having general Formulas (II) and (III).

Structures and the physical constants of several novel compounds of the general Formula (I) are listed in Table 1.

TABLE 1

| No. of examples | Structural formula of compounds | Melting point (° C.) | Retention factor |
|---|---|---|---|
| 1 | | 99–100 | |
| 2 | | oil | 0.31[A] |
| 3 | | 146–147 | |
| 4 | | 148–149 | |

TABLE 1-continued

| No. of examples | Structural formula of compounds | Melting point (° C.) | Retention factor |
|---|---|---|---|
| 5 | | oil | 0.28[A] |
| 6 | | 131–132 | |
| 7 | | 206–207 | |
| 8 | | oil | 0.39[A] |
| 9 | | 109–110 | |
| 10 | | 168–169 | |
| 11 | | amorphous | 0.38[A] |

TABLE 1-continued

| No. of examples | Structural formula of compounds | Melting point (° C.) | Retention factor |
| --- | --- | --- | --- |
| 12 | | 186–187 | |
| 13 | | oil | 0.24[A] |
| 14 | | oil | 0.27[A] |
| 15 | | oil | 0.21[A] |
| 16 | | oil | 0.22[A] |
| 17 | | oil | 0.44[A] |
| 18 | | 183–184 | |
| 19 | | 207–208 | |

TABLE 1-continued

| No. of examples | Structural formula of compounds | Melting point (° C.) | Retention factor |
|---|---|---|---|
| 20 | | 56–62 | |
| 21 | | 138–140 | |
| 22 | | 169–171 | |
| 23 | | 136–137 | |
| 24 | | 130–131 | |
| 25 | | oil | 0.32[A] |
| 26 | | oil | 0.41[A] |

TABLE 1-continued

| No. of examples | Structural formula of compounds | Melting point (° C.) | Retention factor |
|---|---|---|---|
| 27 | | 77–79 | |
| 28 | | 220–222 | |
| 29 | | 224–225 | |
| 30 | | 245–248 | |
| 31 | | 133–134 | |
| 32 | | 220–222 | |
| 33 | | 169–170 | |

TABLE 1-continued

| No. of examples | Structural formula of compounds | Melting point (° C.) | Retention factor |
|---|---|---|---|
| 34 | | 138–139 | |
| 35 | | oil | 0.35[A] |
| 36 | | 68–70 | |
| 37 | | 107–109 | |
| 38 | | amorphous | 0.55[B] |
| 39 | | 105–112 | |
| 40 | | 116–118 | |

TABLE 1-continued

| No. of examples | Structural formula of compounds | Melting point (° C.) | Retention factor |
|---|---|---|---|
| 41 | | oil | 0.63[C] |
| 42 | | oil | 0.22[D] |
| 43 | | oil | .036[C] |
| 44 | | oil | 0.50[C] |
| 45 | | oil | 0.72[C] |
| 46 | | 83–86 | |
| 47 | | oil | 0.72[F] |
| 48 | | oil | 0.70[F] |
| 49 | | 55–60 | |

TABLE 1-continued

| No. of examples | Structural formula of compounds | Melting point (° C.) | Retention factor |
|---|---|---|---|
| 50 | | 60–62 | |
| 51 | | 200–205 | |
| 52 | | 85–90 | |
| 53 | | 122 | |
| 54 | | 107–110 | |
| 55 | | 185–190 | |
| 56 | | 87 | |
| 57 | | 147 | |

TABLE 1-continued

| No. of examples | Structural formula of compounds | Melting point (° C.) | Retention factor |
|---|---|---|---|
| 58 | | 95–100 | |
| 59 | | 250 | |
| 60 | | 155–157 | |
| 61 | | 245 | |
| 62 | | 60 | |
| 63 | | 116 | |
| 64 | | 85 | |
| 65 | | 85 | |

TABLE 1-continued

| No. of examples | Structural formula of compounds | Melting point (° C.) | Retention factor |
|---|---|---|---|
| 66 | | 194 | |
| 67 | | 95 | |
| 68 | | 225–226 | |
| 69 | | 120 | |
| 70 | | 138 | |
| 71 | | 117 | |
| 72 | | 113–118 | |
| 73 | | oil | 0.70[D] |

TABLE 1-continued

| No. of examples | Structural formula of compounds | Melting point (° C.) | Retention factor |
| --- | --- | --- | --- |
| 74 | | 199–202 | |
| 75 | | 197–198 | |
| 76 | | 122–124 | |
| 77 | | 230–232 | |
| 78 | | 95–97 | |
| 79 | | 127–129 | |
| 80 | | 172–173 | |

TABLE 1-continued

| No. of examples | Structural formula of compounds | Melting point (° C.) | Retention factor |
|---|---|---|---|
| 81 | | 204–205 | |
| 82 | | 195–196 | |
| 83 | | oil | 0.20[A] |
| 84 | | 139–140 | |
| 85 | | oil | 0.19[A] |
| 86 | | oil | 0.25[A] |
| 87 | | oil | 0.40[B] |
| 88 | | oil | 0.45[B] |

TABLE 1-continued

| No. of examples | Structural formula of compounds | Melting point (° C.) | Retention factor |
|---|---|---|---|
| 89 | | oil | 0.45[B] |
| 90 | | oil | 0.50[B] |
| 91 | | oil | 0.10[A] |
| 92 | | 62–66 | |
| 93 | | oil | 0.40[E] |
| 94 | | oil | 0.45[E] |
| 95 | | oil | 0.34[A] |
| 96 | | 158–160 | |

TABLE 1-continued

| No. of examples | Structural formula of compounds | Melting point (° C.) | Retention factor |
|---|---|---|---|
| 97 | | 163–164 | |
| 98 | | oil | 0.50[B] |
| 99 | | oil | 0.55[B] |
| 100 | | oil | 0.55[E] |
| 101 | | oil | 0.24[A] |
| 102 | | oil | 0.55[F] |
| 103 | | oil | 0.60[F] |
| 104 | | 70–74 | |

TABLE 1-continued

| No. of examples | Structural formula of compounds | Melting point (° C.) | Retention factor |
|---|---|---|---|
| 105 | | 188–189 | |
| 106 | | 164–165 | |
| 107 | | amorphous | 075[A] |
| 108[a] | | amorphous | 0.26[L] |
| 109[a] | | 142–143 | 0.18[L] |
| 110 | | 163–164 | |
| 111 | | amorphous | 0.34[A] |

TABLE 1-continued

| No. of examples | Structural formula of compounds | Melting point (° C.) | Retention factor |
|---|---|---|---|
| 112 | | amorphous | 0.24[A] |
| 113 | | 96–97 | |
| 114 | | 74–75 | |
| 115 | | 120–123 | |
| 116 | | 195–197 | |
| 117 | | oil | 0.35[A] |

TABLE 1-continued

| No. of examples | Structural formula of compounds | Melting point (° C.) | Retention factor |
|---|---|---|---|
| 118 | | oil | 0.29[A] |
| 119 | | oil | 0.22[A] |
| 120 | | 58–60 | |
| 121 | | 168–169 | |
| 122 | | 105–109 | |
| 123 | | 173–175 | |

TABLE 1-continued
| No. of examples | Structural formula of compounds | Melting point (° C.) | Retention factor |
|---|---|---|---|
| 124 | 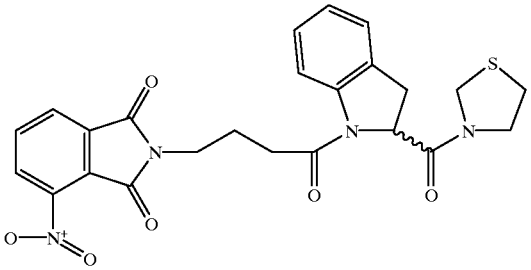 | gradual melting | 0.32[A] |
| 125[b] | 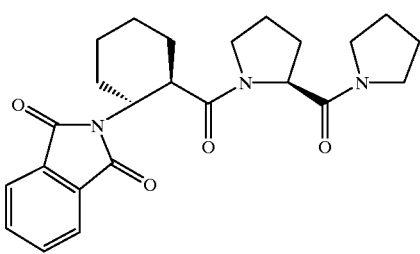 | 188–189 | |
| 126[b] | 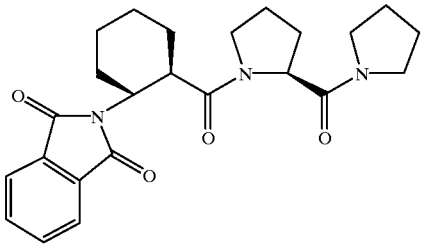 | gradual melting | 0.42[A] |
| 127[c] | 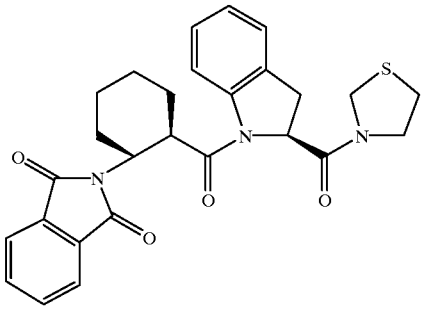 | 127–131 | |
| 128[c] | 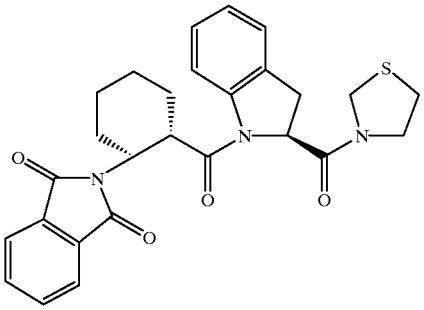 | 181–183 | |

TABLE 1-continued

| No. of examples | Structural formula of compounds | Melting point (° C.) | Retention factor |
|---|---|---|---|
| 129 | | oil | 0.41[A] |
| 130 | | 47–49 | |
| 131 | | amorphous | 0.29[A] |
| 132 | | oil | 0.28[A] |
| 133 | | amorphous | 0.29[A] |
| 134 | | 52 | |
| 135 | | 166–168 | |

TABLE 1-continued

| No. of examples | Structural formula of compounds | Melting point (° C.) | Retention factor |
|---|---|---|---|
| 136 | | 84–85 | |
| 137 | | 103–105 | |
| 138 | | 241–242 | |
| 139 | | >200 | |
| 140[d] | | 78–79 | 0.41[K] |
| 141[d] | | 78–79 | 0.29[K] |

TABLE 1-continued

| No. of examples | Structural formula of compounds | Melting point (°C.) | Retention factor |
|---|---|---|---|
| 142 | | 173–174 | |
| 143 | | 68–72 | |
| 144 | | 80–82 | |
| 145 | | 72–75 | |
| 146 | | 160–165 | |
| 147 | | 260–262 | |

TABLE 1-continued

| No. of examples | Structural formula of compounds | Melting point (° C.) | Retention factor |
| --- | --- | --- | --- |
| 148 | | 140–145 | |
| 149 | | 268–270 | |
| 150 | | 208–211 | |
| 151 | | 236–240 | |
| 152 | | 245–250 | |

TABLE 1-continued

| No. of examples | Structural formula of compounds | Melting point (° C.) | Retention factor |
|---|---|---|---|
| 153 | | 274–280 | |
| 154 | | 172–173 | |
| 155 | | 173 | |
| 156 | | 95–97 | |
| 157 | | 105–107 | |
| 158 | | 137–139 | |

TABLE 1-continued

| No. of examples | Structural formula of compounds | Melting point (° C.) | Retention factor |
| --- | --- | --- | --- |
| 159 | | 201–203 | |
| 160 | | 167–169 | |
| 161 | | 78 | |
| 162 | | 159–160 | |
| 163 | | 221–226 | |

TABLE 1-continued

| No. of examples | Structural formula of compounds | Melting point (° C.) | Retention factor |
| --- | --- | --- | --- |
| 164 | | 246–248 | |
| 165 | | 95 | |
| 166 | | 55–59 | |
| 167 | | 99 | |
| 168 | | 65 | |
| 169 | | 110 | |

TABLE 1-continued

| No. of examples | Structural formula of compounds | Melting point (° C.) | Retention factor |
|---|---|---|---|
| 170 | | 78 | |
| 171 | | 181–184 | |
| 172 | | oil | 0.52[F] |
| 173 | | 114–115 | 0.66[F] |
| 174 | | 94–96 | |
| 175 | | 158–160 | |

TABLE 1-continued

| No. of examples | Structural formula of compounds | Melting point (° C.) | Retention factor |
|---|---|---|---|
| 176 | | 95–100 | |
| 177 | | 217–222 | |
| 178 | | 144 | |

TABLE 1-continued

| No. of examples | Structural formula of compounds | Melting point (° C.) | Retention factor |
|---|---|---|---|
| 179 | | 174–178 | |
| 180 | | 95–105 | |
| 181 | | 132–135 | |
| 182 | | 237–238 | |

TABLE 1-continued
| No. of examples | Structural formula of compounds | Melting point (° C.) | Retention factor |
|---|---|---|---|
| 183 | 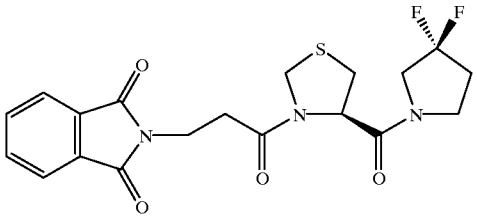 | 137–138 | |
| 184 | 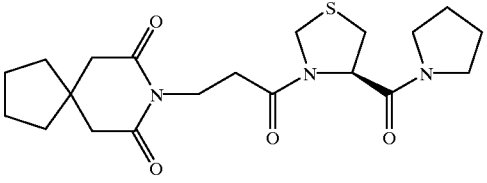 | 148–150 | |
| 185 | 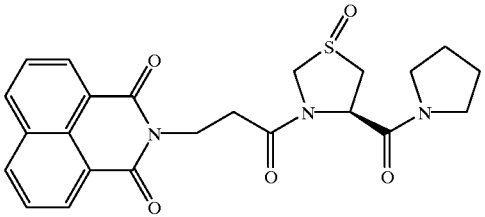 | | 0.26[A] |
| 186 | 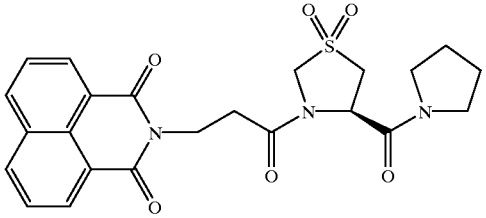 | 191–192 | |
| 187 | 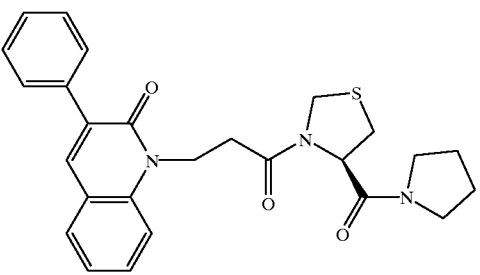 | 176–180 | |

TABLE 1-continued

| No. of examples | Structural formula of compounds | Melting point (° C.) | Retention factor |
|---|---|---|---|
| 188 | 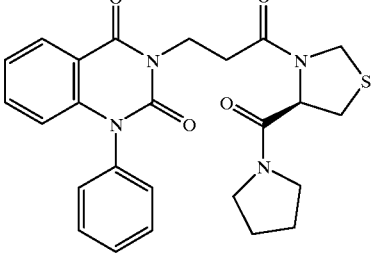 | 143–145 | |
| 189 | 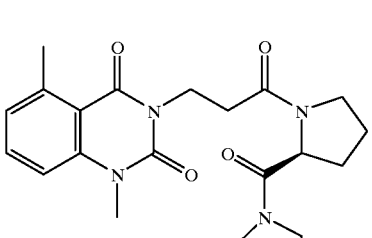 | 178–180 | |
| 190 | 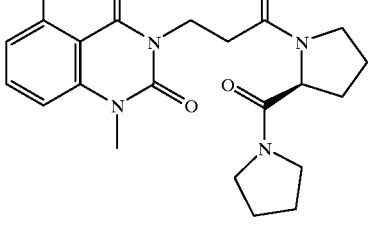 | 181–183 | |
| 191 | 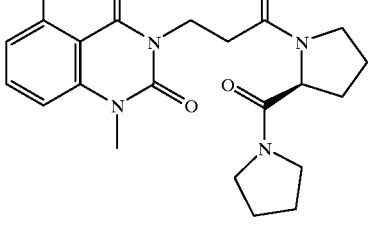 | 95–105 | |

[a, b, c, d]tentative assignment of epimers, maybe reverse
Abbreviations of eluents:
[A]CM201 Chloroform: methanol = 20: 1
[B]BM 41 Benzene methanol = 4: 1
[C]CM 41 Chloroform methanol = 4: 1
[D]DM101 Dichloromethane methanol = 10: 1
[E]CM955 Chloroform methanol = 95: 5
[F]CM 91 Chloroform methanol = 9: 1
[G]DM 91 Dichlormethane methanol = 9: 1
[H]HA 21 n-Hexane acetone = 2: 1
[J]HA 31 n-Hexane acetone = 3: 1
[K]CA 101 Chloroform acetone = 10: 1

What is claimed is:

1. A compound of formula (I)

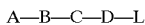   (I)

wherein:

A is formula (I),

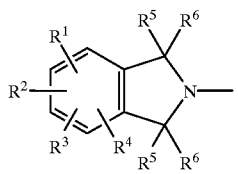   [1]

wherein:

$R^1$, $R^2$, $R^3$ and $R^4$ each is a hydrogen atom, halogen atom, hydroxyl group, straight chain or branched chain alkyl or alkenyl- or alkinyl or alkoxy- or alkenyloxy- or alkinyloxy group consisting of 1–6 carbon atoms, nitro- group, amino group, monoalkylamino or monoacyl- amino group of 1–12 carbon atoms, or dialkylamino- or diacylamino group of 2–24 carbon atoms, where the acyl group is an alkyl, aralkyl, cycloalkyl or aryl type-, cyano group, mercapto group, carboxyl group, esteri- fied carboxyl group of 2–7 carbon atoms, hydroxyalkyl group of 1–6 carbon atoms, acyl group of 1–7 carbon atoms, acyloxy group of 1–7 carbon atoms, phenyl or benzyl group, anilino group, benzoyl group, phenoxy group, benzyloxy group, isocyanato group, isothiocy- anato group, alkylthio group of 1–6 carbon atoms, sulfamino or sulfamoyl group, thiocyanato or cyanato group;

R and $R^6$ each is a hydrogen atom, hydroxyl group, phenyl group or alkyl group of 1–4 carbon atoms or $R^5$ and $R^6$ together is an oxo group;

B is a —$(CH_2)_m$—C(=O)— group, wherein m is an integer of 1 to 21; —O—$(CH_2)_p$—C(=O)— group wherein p is an integer of 1 to 3; or a

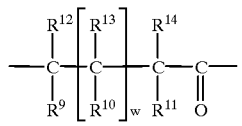

and $R^{14}$ each is a hydrogen alkyl or alkoxy group of 1–6 carbon atoms, halogen, amino group optionally substituted with one or two alkyl groups of 1–6 carbon atoms, or phenyl, phenoxy, aryl-alkyl group of 7–12 carbon atoms or aryl-alkoxy group of 7–12 carbon atoms, each of them optionally are 1, 2 or 3 same or different sub- stituents identical to $R^1$, $R^2$, $R^3$ or $R^4$; or two of $R^9$, $R^{10}$, $R^{11}$, $R^{12}$, $R^{13}$ and $R^{14}$ together is an oxo or epoxy group or further chemical bond or four of them together have two further chemical bonds and the remaining groups are hydrogen atoms; or $R^9$, $R^{10}$, $R^{11}$, $R^{12}$, $R^{13}$ and $R^{14}$ together with the chain carbon atoms is a saturated or unsaturated homocycle of 3–8 carbon atoms or a saturated or unsaturated heterocycle of 2–7 carbon atoms and a nitrogen or sulfur or oxygen atom, to which optionally an aromatic ring of 6–10 carbon atoms is condensed; and w is zero or 1;

C is a prolyl group of formula (37), (39), or (40),

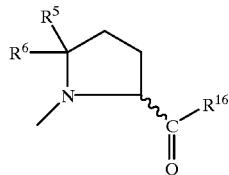   [37]

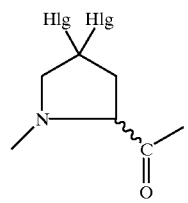   [39]

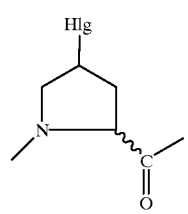   [40]

wherein:

Hlg is a fluorine, chlorine, bromine, or iodine atom;

$R^5$ and $R^6$ are, independently from each other, a hydrogen atom, hydroxyl group, phenyl group or alkyl group of 1–4 carbon atoms; or $R^5$ and $R^6$ together are an oxo-group;

$R^{16}$ is an alkoxy group of 1–4 carbon atoms, or an —NH—$CH_2$—CN group, or an —NH—$CH_2$—$CO_2R^7$ group, where $R^7$ is defined as above; or a D structural unit or an L structural unit; or a group of the formula (44),

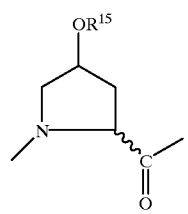   [44]

wherein:

$R^{15}$ is a hydrogen atom, alkyl group of 1–6 carbon atoms, phenyl or naphthyl group;

D is a covalent chemical bond; and

L is a pyrrolidino or 2-cyanopyrrolidino group wherein the pyrrolidino or 2-cyanopyrrolidino group is option- ally substituted by one halogen atom or geminally by two halogen atoms;

and optical, cis-trans, geometric isomers, epimers, tau- tomers or salts thereof.

2. A pharmaceutical composition of one or more com- pounds of the general formula (I) wherein the meanings of A, B, C, D and L are defined in claim 1 and/or optical, cis-trans, geometric isomers, epimers, tautomers, or salts together with a carrier.

3. A process for the preparation of compounds of formula (I) as defined in claim 1 and their optical, cis-trans, geometric isomers, epimers, tautomers and salts, wherein:

a racemic or optically active carboxylic acid of formula (II) is transformed to an acid halide, or an active ester, or to a mixed acid anhydride or to a carbodiimide, and the resulting compound is reacted with a racemic or optically active compound or the salt of formula (III), and the resulted compound of the formula (I) optionally is separated into their optical, cis-trans, geometric isomers, epimers or tautomers or a salt of compounds of formula (I) is formed, or the compounds of formula (I) are liberated from their salts, wherein formula (II) and (III) are defined as

A—B—OH  (II)

H—C—D—L  (III)

4. The compound of claim 1, wherein

A is a group of the general formula (I) wherein $R^1$, $R^2$, $R^3$ and $R^4$ each are a hydrogen atom, halogen atom, amino group or straight chain or branched chain alkyl or alkoxy group of 1–6 carbon atoms, $R^5$ and $R^6$ together is an oxo-group, B is a —$(CH_2)_m$—(CO)— group, wherein m is an integer of 1 to 3;

C is of a prolyl group of formula (37);

L is of a pyrrolidino group optionally geminally substituted by halogen atoms.

5. A process according to claim 3 wherein, an acid addition salt of compound of formula (III) is used.

6. A process according to claim 3 wherein, a reactive mixed anhydride is formed from a compound of formula (II) and pivaloylchloride is applied.

7. A process according to claim 3, wherein the reaction is carried out in an organic solvent.

8. A process according to claim 3, wherein the reaction is carried out at a temperature between −25° C. and the boiling point of the reaction mixture.

9. A process according to claim 3, wherein the reaction is carried out in the presence of an acid binding agent.

* * * * *